(12) United States Patent
Kim et al.

(10) Patent No.: US 11,446,281 B2
(45) Date of Patent: Sep. 20, 2022

(54) ANTI-INFLAMMATORY COMPOSITION COMPRISING ACYLHYDRAZONE DERIVATIVE

(71) Applicant: KOREA RESEARCH INSTITUTE OF BIOSCIENCE AND BIOTECHNOLOGY, Daejeon (KR)

(72) Inventors: Bo Yeon Kim, Daejeon (KR); Joonsung Hwang, Daejeon (KR); Nak Kyun Soung, Daejeon (KR); Jong Seog Ahn, Daejeon (KR); Kyung Ho Lee, Daejeon (KR); Jiyun Mun, Daejeon (KR); Srinivasrao Ganipisetti, Daejeon (KR); Hyunjoo Cha, Daejeon (KR); Mija Ahn, Daejeon (KR); Hee Gu Lee, Daejeon (KR); Jae-Hyuk Jang, Daejeon (KR); In Ja Ryoo, Daejeon (KR); Sung-Kyun Ko, Daejeon (KR)

(73) Assignee: Korea Research Institute Of Bioscience And Biotechnology, Daejeon (KR)

( * ) Notice: Subject to any disclaimer, the term of this patent is extended or adjusted under 35 U.S.C. 154(b) by 0 days.

(21) Appl. No.: 16/966,162

(22) PCT Filed: Jan. 11, 2019

(86) PCT No.: PCT/KR2019/000482
§ 371 (c)(1),
(2) Date: Jul. 30, 2020

(87) PCT Pub. No.: WO2019/151676
PCT Pub. Date: Aug. 8, 2019

(65) Prior Publication Data
US 2021/0030716 A1 Feb. 4, 2021

(30) Foreign Application Priority Data

Jan. 30, 2018 (KR) .................. 10-2018-0011046

(51) Int. Cl.
*A61K 31/4045* (2006.01)
*A61P 17/00* (2006.01)
*C07D 405/12* (2006.01)
*A61P 29/00* (2006.01)

(52) U.S. Cl.
CPC .......... *A61K 31/4045* (2013.01); *A61P 17/00* (2018.01); *A61P 29/00* (2018.01)

(58) Field of Classification Search
CPC ...... A61K 31/4045; A61P 17/00; A61P 29/00; C07D 405/12
See application file for complete search history.

(56) References Cited

U.S. PATENT DOCUMENTS

| 5,244,917 A | 9/1993 | Petraitis et al. |
| 8,084,456 B2 * | 12/2011 | Burns .................. C07D 405/12 514/255.06 |
| 2015/0182502 A1 * | 7/2015 | Kim ....................... A61P 35/00 514/414 |

FOREIGN PATENT DOCUMENTS

WO 2005/037773 4/2005

OTHER PUBLICATIONS

Diakos et al (Lancet Oncol, 2014; 15:e493-503) (Year: 2014).*
(Continued)

*Primary Examiner* — Marcos L Sznaidman
*Assistant Examiner* — Rayna Rodriguez
(74) *Attorney, Agent, or Firm* — Lex IP Meister, PLLC

(57) ABSTRACT

The present invention relates to a composition for preventing, alleviating or treating inflammatory diseases, comprising, as an active ingredient, an acylhydrazone derivative compound, a stereoisomer thereof or a pharmaceutically acceptable salt thereof. an acylhydrazone derivative com- (Continued)

pound, a stereoisomer thereof or a pharmaceutically acceptable salt thereof, of the present invention, effectively inhibits inflammatory cytokines and inflammatory signaling pathways, thereby effectively alleviating symptoms of inflammatory diseases such as dermatitis. Therefore, the composition according to the present invention may be effectively used for the prevention, alleviation or treatment of inflammatory diseases.

14 Claims, 9 Drawing Sheets

(56) References Cited

OTHER PUBLICATIONS

Freire et al (Periodontol 2000, 2013; 63(1):149-164) (Year: 2013).*
Tabas et al (Science, 2013; 339(6116):166-172) (Year: 2013).*
EPO, Search Report of EP 19747010.7 dated Nov. 29, 2021.
Seyedeh Sara Mirfazli et al., "N-Substituted indole carbohydrazide derivatives: synthesis and evaluation of their antiplatelet aggregation activity", Daru Journal of Pharmaceutical Sciences, Biomed Central LTD, London, UK, vol. 22, No. 1, Sep. 20, 2014, p. 65.
Maqsood Ahmad Malik et al., "Synthesis, Structure Optimization and Antifungal Screening of Novel Tetrazole Ring Bearing Acyl-Hydrazones", International Journal of Molecular Sciences, vol. 13, No. 9, Sep. 1, 2012, pp. 10880-10898.
Ana Daura Travassos de Oliveira Moraes et al., "Synthesis, in vitro and in vivo biological evaluation, COX-1 /2 inhibition and molecular docking study of indole-N-acyl hydrazone derivatives", Bioorganic, vol. 26, No. 20, Nov. 1, 2018, pp. 5388-5396.
Davidson M.S. Wanderley et al., "Biocompatibility and mechanical properties evaluation of chitosan films containing an N-acylhydrazonic derivative", Eur J Pharm Sci. Dec. 1, 2020;155:105547. doi: 10.1016/j.ejps.2020.105547. Epub Sep. 11, 2020.

* cited by examiner

ANTI-INFLAMMATORY COMPOSITION COMPRISING ACYLHYDRAZONE DERIVATIVE

TECHNICAL FIELD

The present disclosure relates to a composition for preventing, alleviating, or treating inflammatory diseases comprising a compound represented by a Chemical Formula 1, a stereoisomer thereof or a pharmaceutically acceptable salt thereof as an active ingredient.

BACKGROUND ART

Atopic dermatitis is a chronic skin disease that occurs frequently in modern people and has a medically unknown cause. Atopic dermatitis is generally known as a disease caused by an imbalance in the human immune system. In recent years, the onset of atopic dermatitis in a domestic region and abroad has been widespread from children to adults, and thus an effective treatment agent for the atopic dermatitis is required.

Currently, steroid-based atopic dermatitis inhibitors are used as therapeutic agents. However, due to the absence of a diagnostic method capable of accurately diagnosing pathogenesis of atopic dermatitis and lack of a corresponding accurate customized treatment scheme, a temporary alleviating effect rather than a fundamental solution of the atopic dermatitis is realized. At the same time, resistance thereto occurs. Therefore, there is an urgent need to develop a drug that may be excellent in immunological treatment and anti-inflammatory efficacy and may have few side effects and thus may be used for a long time.

On the other hand, Korean Patent Application Publication No. 10-2014-0032916 has disclosed that N-methylenenaphtho[2,1-b]furan-2-carbohydrazide derivative significantly inhibits cell mitosis and acts effectively on cancer cells having multi-drugs resistance. In addition, Korean Patent Application Publication No. 10-2017-0098170 discloses an indole derivative compound showing an inhibitory effect on cancer cell proliferation with improved stability and solubility. The above documents disclose that the acylhydrazone derivative compounds may be effectively used to inhibit proliferation of some cancer cells, but do not disclose any inhibitory effect of inflammatory diseases.

DISCLOSURE

Technical Problem

The present inventors have studied to develop an agent for effective prevention and treatment of inflammatory diseases. As a result, we have identified that acylhydrazone derivative compounds have excellent anti-inflammatory effects in inflammatory-induced animal models and cell line models and thus may be used for prevention or treatment of inflammatory diseases. In this way, the present disclosure has been completed.

Technical Solution

In order to achieve the above object, one aspect of the present disclosure provides a pharmaceutical composition for preventing or treating inflammatory diseases comprising an acylhydrazone derivative compound, a stereoisomer thereof or a pharmaceutically acceptable salt thereof as an active ingredient.

Another aspect of the present disclosure provides a food composition for preventing or alleviating inflammatory diseases comprising the compound or the stereoisomer thereof as an active ingredient.

Another aspect of the present disclosure provides a cosmetic composition for preventing or alleviating dermatitis comprising the compound or the stereoisomer thereof as an active ingredient.

Another aspect of the present disclosure provides a use of the pharmaceutical composition for preventing or treating inflammatory diseases.

Another aspect of the present disclosure provides a use of the pharmaceutical composition for preparing a medicament for prevention or treatment of inflammatory diseases.

Another aspect of the present disclosure provides a method for preventing or treating inflammatory diseases, the method including administering the pharmaceutical composition.

Another aspect of the present disclosure provides a use of the cosmetic composition for preventing or alleviating dermatitis.

Another aspect of the present disclosure provides a use of the cosmetic composition for preparing cosmetic products for preventing or alleviating dermatitis.

Another aspect of the present disclosure provides a method for preventing or alleviating dermatitis, the method including administering the cosmetic composition.

Advantageous Effects

The acylhydrazone derivative compound, the stereoisomer thereof or the pharmaceutically acceptable salt thereof according to the present disclosure effectively suppresses inflammatory cytokines and inflammatory signaling pathways, thereby effectively alleviating symptoms of inflammatory diseases such as dermatitis. Therefore, the composition according to the present disclosure may be usefully used for the prevention, alleviation, or treatment of inflammatory diseases.

MODES OF THE INVENTION

Figure 1:
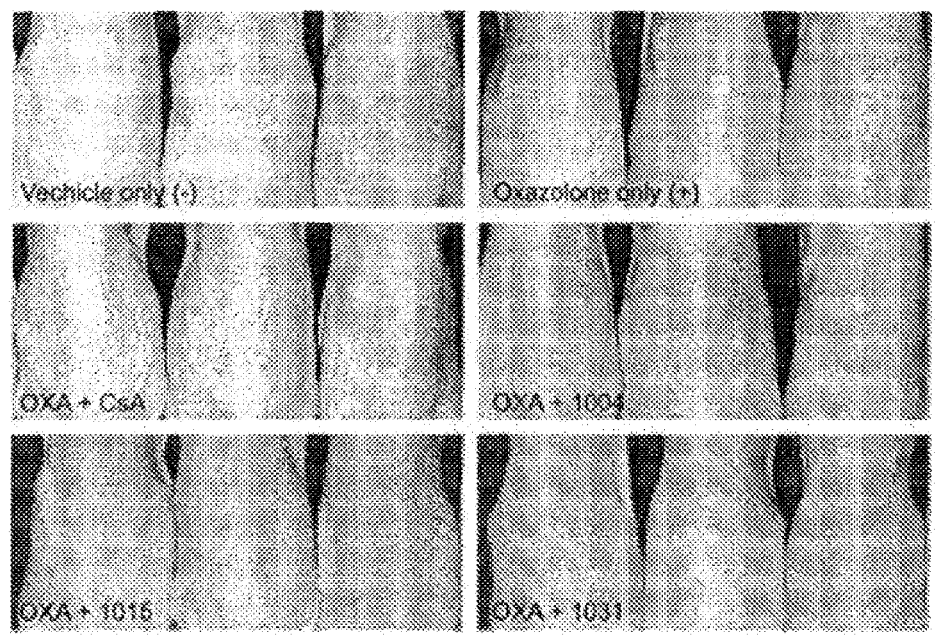
FIG. 1 is a figure visually identifying an effect of the acylhydrazone derivative compound on dermatitis suppression using mice having induced dermatitis on a back portion thereof.

Hereinafter, the present disclosure will be described in detail. Each description and embodiment as disclosed in the present disclosure may be applied to other descriptions and embodiments. That is, all combinations of various elements disclosed in the present disclosure fall within a scope of the present disclosure. In addition, the scope of the present disclosure may not be considered to be limited to specific descriptions described below.

The present disclosure provides a pharmaceutical composition for preventing or treating inflammatory diseases comprising an acylhydrazone derivative compound represented by a following Chemical Formula 1, a stereoisomer thereof, or a pharmaceutically acceptable salt thereof as an active ingredient.

[Chemical Formula 1]

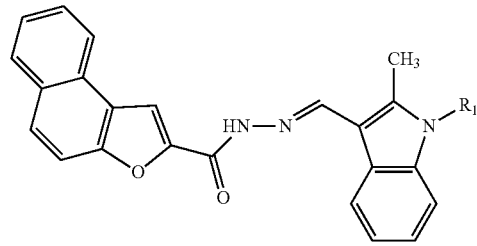

In the Chemical Formula 1, $R_1$ represents $C_1$ to $C_4$ alkyl or $-(CH_2)_m(C=O)OR_2$, and $R_2$ represents $C_1$ to $C_4$ alkyl, and m is 0, 1, 2 or 3. Specifically, $R_1$ may be methyl, ethyl, propyl or butyl. Further, $R_1$ may be $-(C=O)OR_2$ when m is 0, may be $-(CH_2)(C=O)OR_2$ when m is 1, and may be $-(CH_2)_2(C=O)OR_2$ when m is 2, and may be $-(CH_2)_3(C=O)OR_2$ when m is 3. In addition, $R_2$ may be methyl, ethyl, propyl or butyl.

According to an embodiment of the present disclosure, $R_1$ in the compound represented by Chemical Formula 1 may be methyl. According to another embodiment of the present disclosure, $R_2$ in the compound represented by the Chemical Formula 1 may be methyl or ethyl.

In one embodiment of the present disclosure, the compound represented by the Chemical Formula 1 may include a compound represented by a following Chemical Formula 2:

[Chemical Formula 2]

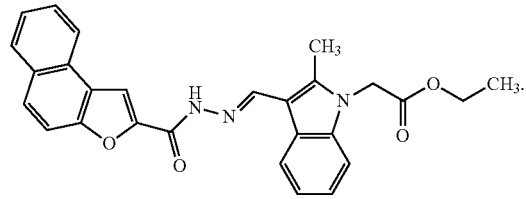

The compound represented by the Chemical Formula 2 may be named as ethyl(2-methyl-3(E)-{[(naphtho[2,1-b]furan-2-ylcarbonyl)hydrazono]methyl}-1H-indole-1-yl)acetate, and is referred herein simply to as WCI-1004.

In one embodiment of the present disclosure, the compound represented by the Chemical Formula 1 may include a compound represented by a following Chemical Formula 3:

[Chemical Formula 3]

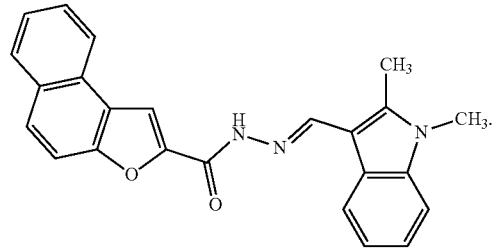

The compound represented by the Chemical Formula 3 may be named as (E)-N'-(1,2-dimethyl-1H-indole-3-yl)

methylene)naphtho[2,1-b]furan-2-carbohydrazide, and is briefly referred herein to as WCI-1015.

In one embodiment of the present disclosure, the compound represented by the Chemical Formula 1 may include a compound represented by a following Chemical Formula 4:

[Chemical Formula 4]

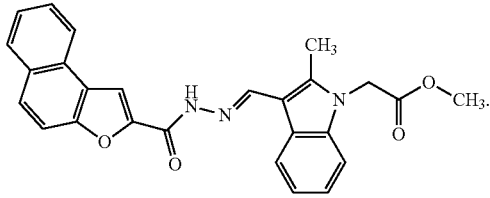

The compound represented by the Chemical Formula 4 may be named as methyl(E)-2-(2-methyl-3-((2-(naphtho[2,1-b]furan-2-carbonyl)hydrazono)methyl)-1H-indole-1-yl) acetate, and is briefly referred herein to as WCI-1031.

In the present disclosure, the compound represented by the Chemical Formula 1 may be prepared, for example, by a method disclosed in Korean Patent Application Publication No. 10-2017-0098170. However, the present disclosure is not limited thereto.

In the present disclosure, the pharmaceutically acceptable salt means a salt commonly used in the pharmaceutical industry. For example, the pharmaceutically acceptable salt may include inorganic ionic salts made of calcium, potassium, sodium and magnesium, inorganic acid salts made of hydrochloric acid, nitric acid, phosphoric acid, bromic acid, iodic acid, perchloric acid, and sulfuric acid, organic acid salts made of acetic acid, trifluoroacetic acid, citric acid, maleic acid, succinic acid, oxalic acid, benzoic acid, tartaric acid, fumaric acid, mandelic acid, propionic acid, citric acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, sulfonates made of methanesulfonic acid, ethanesulfonic acid, benzenesulfonic acid, p-toluenesulfonic acid and naphthalenesulfonic acid, amino acid salts made of glycine, arginine, lysine, etc., and amine salts made of trimethylamines, triethylamine, ammonia, pyridine, picoline, and the like. However, the types of salts indicated in the present disclosure are not limited to the salts as listed.

The compound represented by the Chemical Formula 1 in the present disclosure may contain one or more asymmetric carbons. Accordingly, the compound represented by the Chemical Formula 1 may be present in a form of racemates, racemic mixtures, single enantiomers, diastereomeric mixtures and individual diastereomers. These isomers, for example, the compounds represented by the Chemical Formula 1 may be separated using a tube chromatography or HPLC. Alternatively, the stereoisomer of each of the compounds represented by the Chemical Formula 1 may be stereo-specifically synthesized using an optically pure starting material and/or reagent of a known arrangement.

The acylhydrazone derivative compound represented by the Chemical Formula 1 according to the present disclosure, the stereoisomer thereof, or the pharmaceutically acceptable salt thereof may be useful for the prevention or treatment of inflammatory diseases.

The term "inflammatory diseases" as used herein refers to a condition characterized by one or more of pain (pain due to production of harmful substances and due to nerve stimulation), fever (fever due to vasodilation), redness (redness due to vasodilation and increased blood flow), swelling (tumors due to excessive fluid inflow or limited outflow), and a malfunction (partial or complete, temporary or permanent loss of function). Non-limiting examples of the inflammatory diseases to which the compounds of the Chemical Formula 1 according to the present disclosure may be applied may include dermatitis, allergies, psoriasis, eczema, pruritus, itching of the skin, hives, idiopathic chronic urticaria, scleroderma, nasal polyps, rhinitis, chronic sinusitis, nasal congestion, nasal itching, asthma, chronic obstructive pulmonary disease, rheumatoid arthritis, conjunctivitis, keratoconjunctivitis, ophthalmitis, dry eye, heart failure, arrhythmia, atherosclerosis, multiple sclerosis, inflammatory bowel disease, inflammatory pain, neuropathic pain, osteoarthritis pain, and thyroid autoimmune diseases. However, the present disclosure is not limited thereto.

In one embodiment of the present disclosure, the inflammatory diseases may be dermatitis. In the present disclosure, the dermatitis may include atopic dermatitis, contact dermatitis, allergic dermatitis, acne, eczema, rosacea, psoriasis and oily skin and contact infectious impetigo. However, the present disclosure is not limited thereto.

In one embodiment of the present disclosure, the dermatitis may be atopic dermatitis. In the present disclosure, the term atopic dermatitis refers to a chronic skin disorder that is inflammatory, recurrent, non-infectious, and causes pruritis, and is often associated with other atopic disorders such as allergic rhinitis and asthma. Certain forms of atopic dermatitis named based on a place where they occur or their appearance or stressors that cause them are also included in the atopic dermatitis in the present disclosure. Atopic dermatitis shows symptoms such as dry eczema skin, papules, and severe itching. Epithelial hyperplasia, epidermal hyperplasia and accumulation of lymphocytes and mast cells are identified in lesion samples of atopic dermatitis patients. Patients with atopic dermatitis generally suffer from severe itching, thereby causing inflammation of skin lesions to further exacerbate itching and worsen clinical symptoms.

Figure 3A:
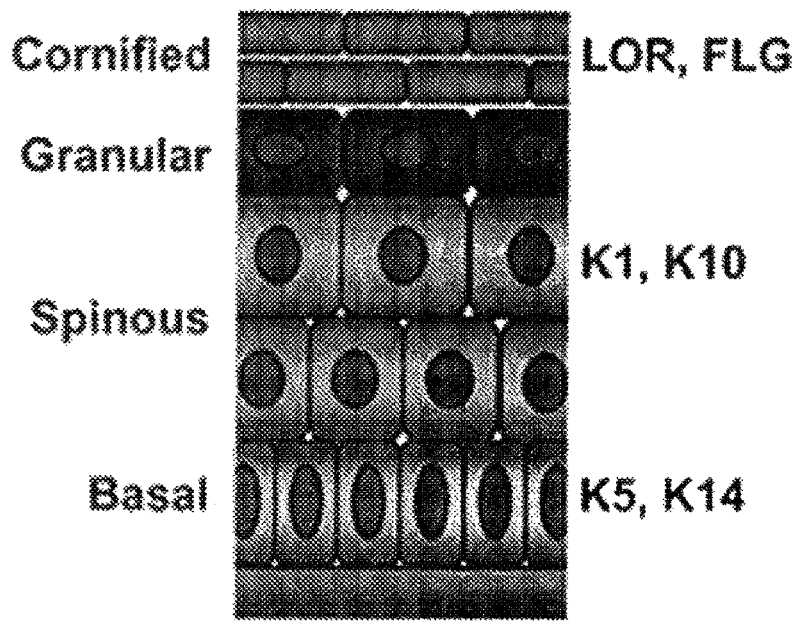
FIG. 3A is a figure showing a base layer, a stratum spinosum, a granular layer and a stratum corneum constituting an epidermis and an expression marker of each of the layers.
Figure 3B:
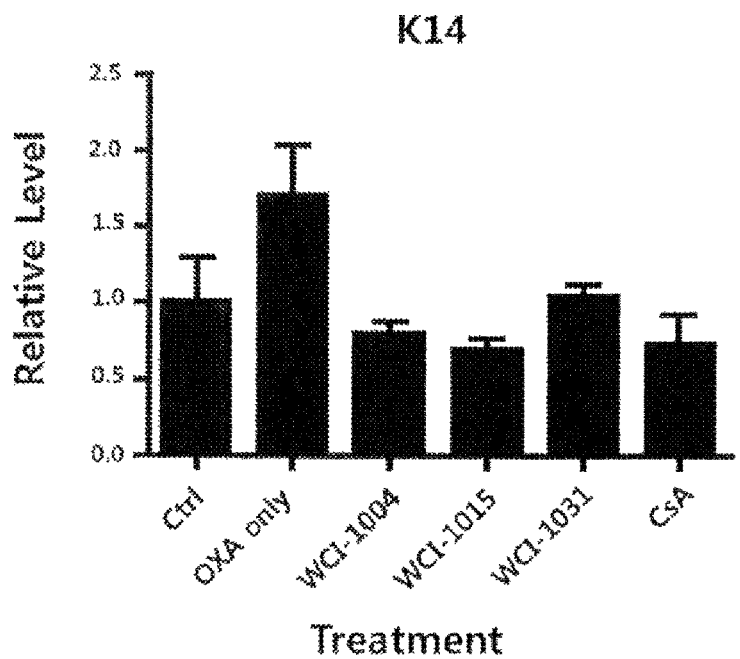
FIG. 3B is a figure showing an expression level of K14 (Keratin 14) in a skin tissue after administration of the acylhydrazone derivative compound or Cyclosporine A to mice having induced dermatitis on a back portion thereof.
Figure 3C:
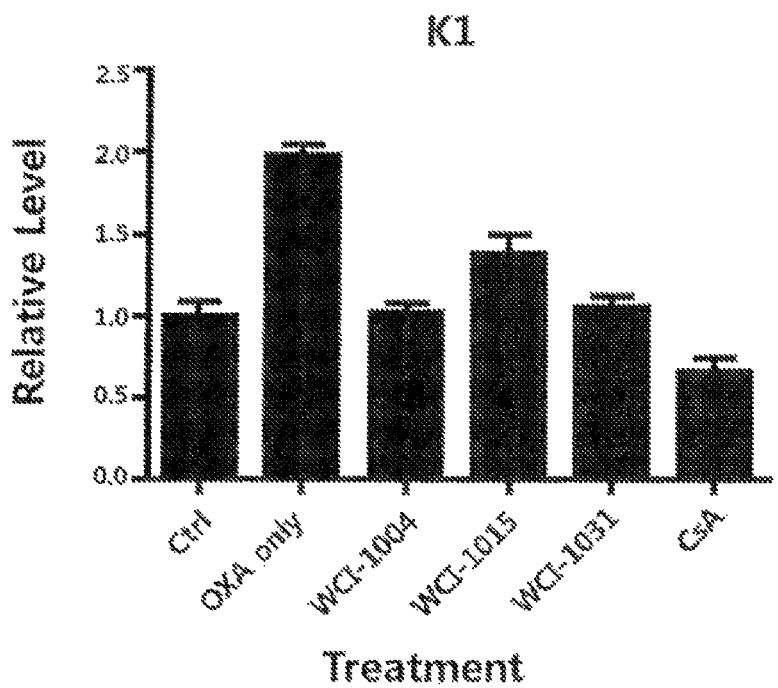
FIG. 3C is a figure showing an expression level of K1 (Keratin 1) in a skin tissue after administration of the acylhydrazone derivative compound or Cyclosporine A to mice having induced dermatitis on a back portion thereof.
Figure 3D:
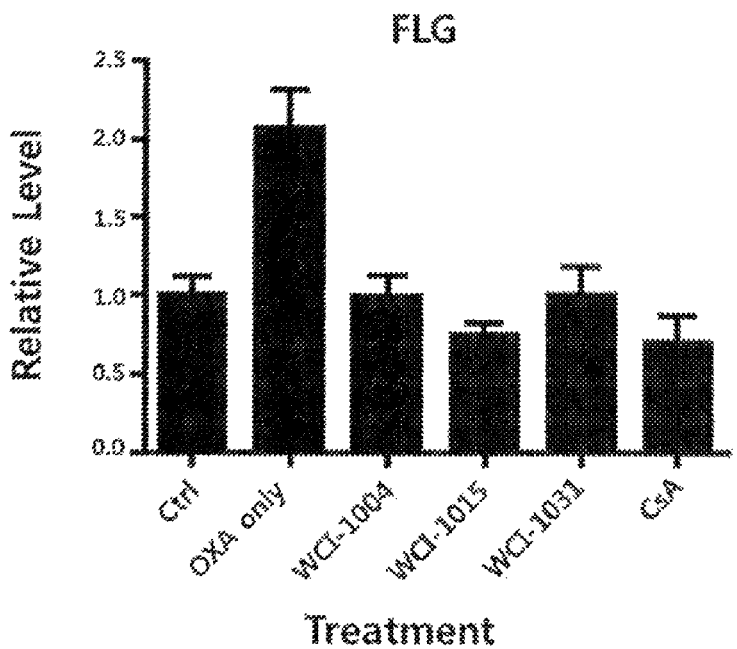
FIG. 3D is a figure showing an expression level of FLG (Filaggrin gene) in a skin tissue after the acylhydrazone derivative compound or Cyclosporine A is administered to a mouse having induced dermatitis on a back portion thereof.
Figure 4:
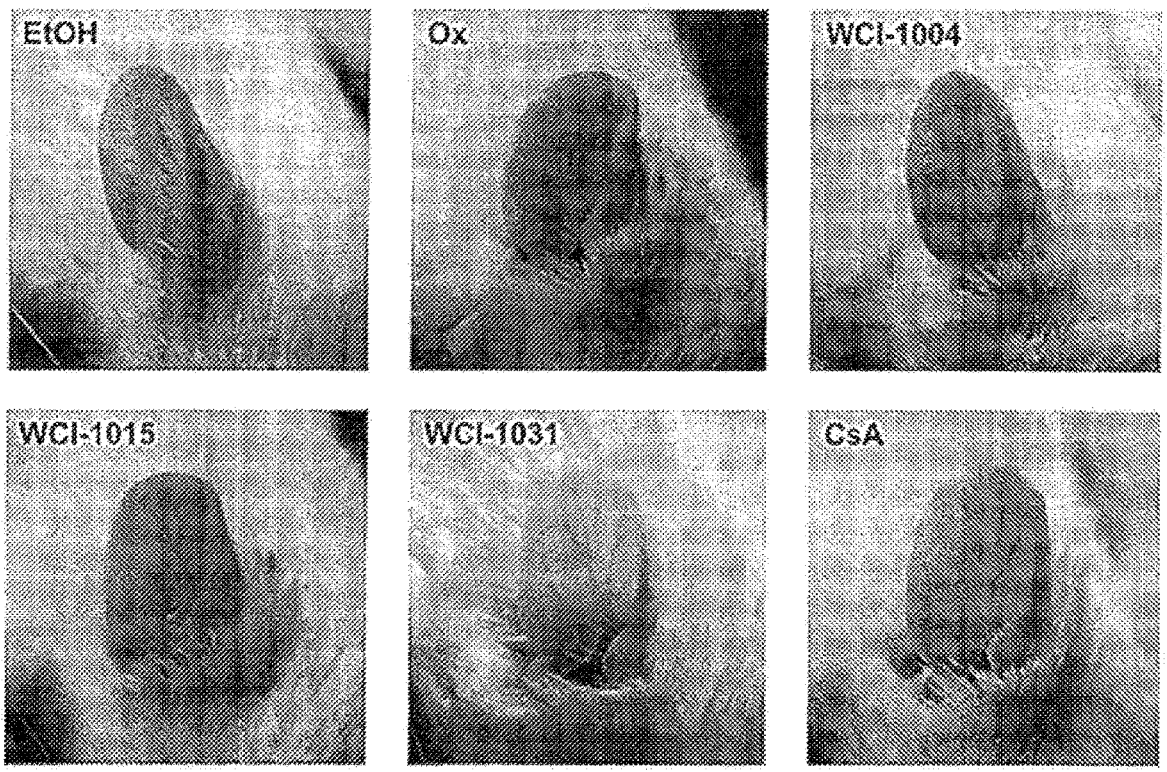
FIG. 4 is a figure visually identifying an effect of the acylhydrazone derivative compound on dermatitis suppression using a mouse having induced dermatitis in an ear.
Figure 8A:
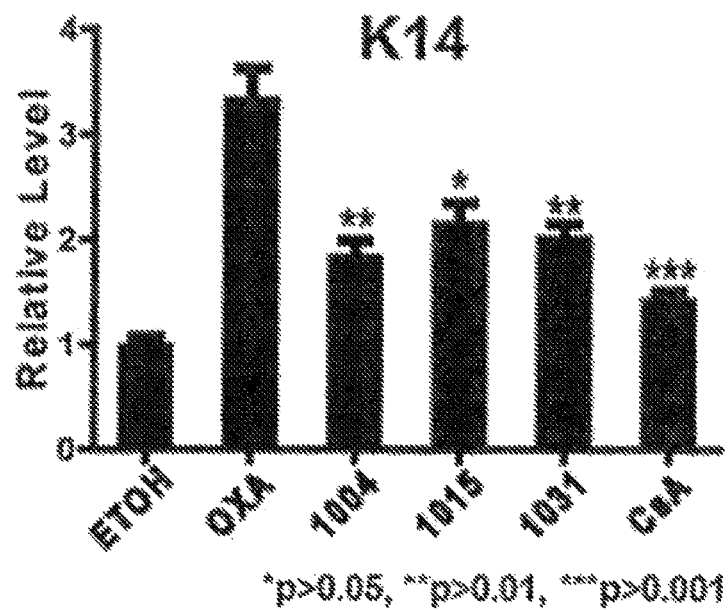
FIG. 8A is a figure showing an expression level of K14 in a skin tissue after the acylhydrazone derivative compound or Cyclosporine A is administered to mice having induced dermatitis in an ear.
Figure 8B:
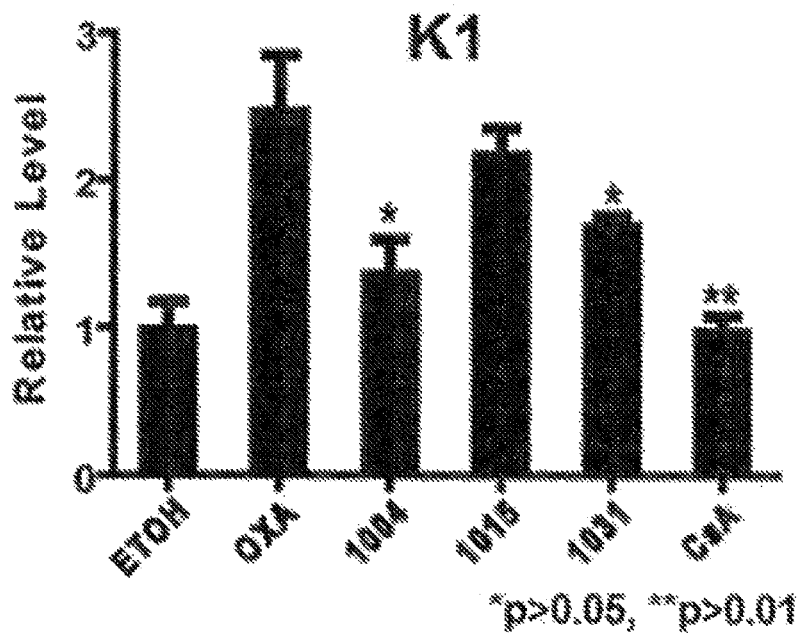
FIG. 8B is a figure showing an expression level of K1 in a skin tissue after the acylhydrazone derivative compound or Cyclosporine A is administered to mice having induced dermatitis in an ear.
Figure 9:
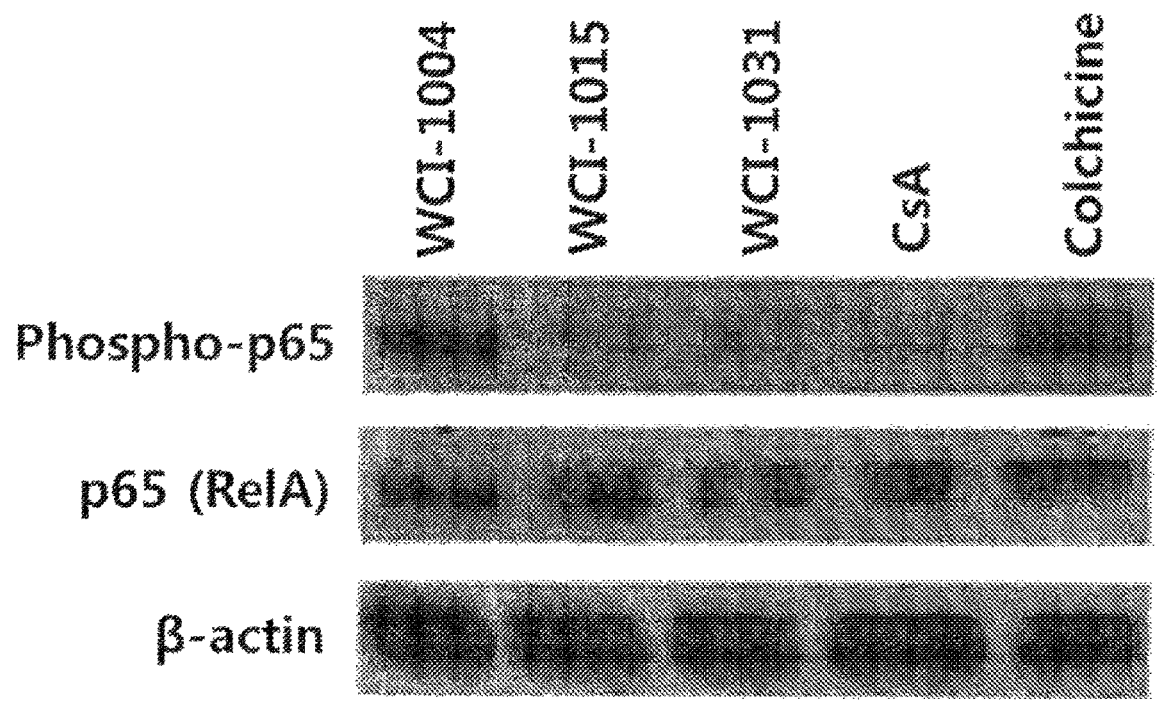
FIG. 9 is a figure identifying an inhibitory effect of an inflammatory signaling pathway by the acylhydrazone derivative compound using immune cell lines.

In an embodiment of the present disclosure, the compound represented by the Chemical Formula 1 suppresses skin erythema and skin dryness in dermatitis-induced animal models (FIG. 1 and FIG. 4). It has been identified that the compound represented by the Chemical Formula 1 effectively suppresses an expression of inflammatory cytokines and epithelial hyperplasia symptom (FIG. 2A to FIG. 2C, FIG. 3A to FIG. 3D, FIG. 6A to FIG. 6C, and FIG. 8A and FIG. 8B), and effectively inhibits the inflammatory signaling pathway in immune cell lines (FIG. 9). Thus, it has been identified that the compound represented by the Chemical Formula 1 may be usefully used as a therapeutic agent for inflammatory diseases including dermatitis.

In the present disclosure, the term "inflammatory cytokine" refers to a cytokine that causes an inflammatory reaction occurring in the body, and is used in a common sense in the technical field to which the present disclosure belongs. For example, IL-2, IL-4, and IL-13 may act as inflammatory cytokines to induce dermatitis.

The pharmaceutical composition may further contain one or more active ingredients exhibiting anti-inflammatory activity.

The pharmaceutical composition may further contain a pharmaceutically acceptable additive. In this connection, the pharmaceutically acceptable additives may include starch, gelatinized starch, microcrystalline cellulose, milk sugar, povidone, colloidal silicon dioxide, calcium hydrogen phosphate, lactose, mannitol, starch syrup candy, gum arabic, pregelatinized starch, corn starch, powdered cellulose, hydroxypropyl cellulose, opadry, sodium starch glycolate, lead carnauba, synthetic aluminum silicate, stearic acid, magnesium stearate, aluminum stearate, calcium stearate, white sugar, dextrose, sorbitol and talc. It is preferable that the pharmaceutically acceptable additive according to the present disclosure is contained at 0.1 to 90 parts by weight based on a weight of the composition. However, the present disclosure is not limited thereto.

The pharmaceutical composition may be formulated in various formulations for oral and parenteral administration in actual clinical administration. In the formulation, the formulations may be prepared using diluents or excipients such as fillers, extenders, binders, wetting agents, disintegrating agents, surfactants, etc., which are usually used. Solid preparations for oral administration may include tablets, pills, powders, granules, capsules, and the like. These solid preparations may be prepared by mixing one or more excipients, such as starch, calcium carbonate, sucrose, lactose, or gelatin with the common carpesium extract. Moreover, in addition to simple excipients, lubricants such as magnesium stearate talc may also be used. Liquid preparations for oral use may include suspensions, intravenous solutions, emulsions and syrups. The liquid preparations may contain water and liquid paraffin as commonly used simple diluents, and various excipients, such as wetting agents, sweeteners, fragrances, and preservatives. Preparations for parenteral administration may include sterile aqueous solutions, non-aqueous solvents, suspensions, emulsions, lyophilized preparations, and suppositories. A non-aqueous solvent and a suspension solvent may include propylene glycol, polyethylene glycol, vegetable oil such as olive oil, and injectable ester such as ethyl oleate. A base for suppositories may include witepsol, macrogol, tween 61, cacao butter, laurin butter, glycerogelatin, and the like.

The pharmaceutical composition may be administered orally or parenterally depending on a desired method. For parenteral administration, transdermal administration, external application to the skin, intraperitoneal injection, intrarectal injection, subcutaneous injection, intravenous injection, intramuscular injection or intrathoracic injection may be selected. For example, transdermal administration may be selected. A dosage range varies according to the patient's weight, age, sex, health status, diet, an administration time, an administration method, an excretion rate, and severity of the disease.

The pharmaceutical composition may be administered in a pharmaceutically effective amount. In the present disclosure, the expression "pharmaceutically effective amount" means an amount sufficient to treat the disease at a reasonable benefit/risk ratio applicable to medical treatment. The effective amount may be determined based on a type of a patient's disease, severity thereof, activity of a drug, sensitivity to the drug, an administration time, an administration route and a discharge rate, a treatment duration, a drug used concurrently, and other factors well known in the medical field.

The composition according to the present disclosure may be administered as an individual therapeutic agent or in combination with other therapeutic agents, and may be administered sequentially or simultaneously with a conventional therapeutic agent, and may be administered in a single time or multiple times. Considering all of the above factors, it is important to administer an amount thereof selected such that a maximum effect is achieved in a minimal amount without side effects. An appropriate amount may be easily determined by a person skilled in the art.

Specifically, the effective amount of the compound according to the present disclosure may vary depending on the patient's age, sex and weight. In general, 0.1 mg to 100 mg per kg body weight, preferably 0.5 mg to 10 mg per kg body weight may be administered daily, every other day, or 1 to 5 times a week or 1 to 5 times a day. However, since the dosage may be increased or decreased depending on the route of administration, severity of the disease, sex, weight, and age of the patient, the dosage does not limit the scope of the present disclosure in any way.

Since the compound represented by the Chemical Formula 1 according to the present disclosure exhibited excellent anti-inflammatory activity in a dermatitis-induced mouse model comprising the compound as an active ingredient may be useful as a food composition for preventing or alleviating inflammation.

The food composition may further contain other food compositions, health functional foods or additives typically used in beverages.

For example, the food composition may contain white sugar, fructose, glucose, D-sorbitol, mannitol, isomaltooligosaccharide, stevioside, aspartame, acesulfame potassium, sweetening agents such as sucralose, acidifying agents such as citric anhydride, DL-apple acid, succinic acid and salts thereof, preservatives such as benzoic acid and derivatives thereof, various nutrients, vitamins, minerals (electrolytes), flavors such as synthetic flavors and natural flavors, colorants and neutralizers (cheese, chocolate, etc.), pectic acid and salts thereof, alginic acid and salts thereof, organic acids, protective colloidal thickeners, pH adjusting agents, stabilizers, preservatives, glycerin, alcohols, carbonic acid used in carbonated beverages, and the like. Moreover, the food composition may contain fruit flesh for the preparation of natural fruit juices and vegetable drinks. A content of these additives may be in a range of about 20 parts by weight or smaller based on 100 parts by weight of the food composition according to the present disclosure.

When the food composition is a beverage, the food composition may further contain a flavoring agent or natural carbohydrates that are usually contained in the beverage. The natural carbohydrate may include monosaccharides such as glucose and fructose, disaccharides such as maltose and sucrose, polysaccharides such as dextrin and cyclodextrin, or sugar alcohols such as xylitol, sorbitol and erythritol. Moreover, the flavoring agent may include a natural flavoring agent of thaumatin or stevia extract (rebaudioside A, glycyrrhizin) or a synthetic flavoring agent such as saccharin or aspartame. When the food composition is a beverage, natural carbohydrates may be generally contained therein in an amount of about 1 g to 20 g, preferably about 5 g to 12 g based on 100 ml of the composition.

The food composition may be prepared in the form of a powder, granule, tablet, capsule, or beverage, which in turn may be used as foods, beverages, gums, teas, vitamin complexes, and health supplements.

Moreover, since the compound represented by the Chemical Formula 1 of the present disclosure exhibited excellent inflammatory inhibitory activity in a mouse model having induced dermatitis comprising the compound as an active ingredient may be useful as a cosmetic composition for preventing or alleviating dermatitis.

The cosmetic composition may be prepared into any formulation conventionally manufactured in the art. For example, the cosmetic composition may be formulated into a solution, suspension, emulsion, paste, gel, cream, lotion, powder, soap, surfactant-containing cleansing, oil, powder foundation, emulsion foundation, wax foundation and spray, etc. However, the present disclosure is not limited thereto. More specifically, the cosmetic composition may be prepared in the form of flexible lotion, nutrition lotion, nutrition cream, massage cream, essence, eye cream, cleansing cream, cleansing foam, cleansing water, pack, spray or powder.

When the formulation of the cosmetic composition is a paste, cream or gel, animal oil, vegetable oil, wax, paraffin, starch, tragacanth, cellulose derivative, polyethylene glycol, silicone, bentonite, silica, talc or zinc oxide may be used as carrier components.

When the formulation of the cosmetic composition is a powder or spray, lactose, talc, silica, aluminum hydroxide, calcium silicate or polyamide powder may be used as a carrier component. In particular, when the formulation of the cosmetic composition is a spray, the formation may additionally contain a propellant such as chlorofluorohydrocarbon, propane/butane or dimethyl ether.

When the formulation of the cosmetic composition is a solution or emulsion, a solvent, solubilizing agent or emulsifying agent is used as a carrier component. Examples thereof may include water, ethanol, isopropanol, ethyl carbonate, ethyl acetate, benzyl alcohol, benzyl benzoate, propylene glycol, 1,3-butylglycol oil, glycerol aliphatic esters, polyethylene glycol or fatty acids ester of sorbitan.

When the formulation of the cosmetic composition is a suspension, a carrier component may include liquid diluents such as water, ethanol or propylene glycol, suspensions such as ethoxylated isostearyl alcohol, polyoxyethylene sorbitol ester and polyoxyethylene sorbitan ester, microcrystalline cellulose, aluminum metahydroxide, bentonite, agar or tragacanth, etc.

When the formulation of the cosmetic composition is a surfactant-containing cleansing cosmetic, the carrier component may include aliphatic alcohol sulfate, aliphatic alcohol ether sulfate, sulfosuccinic acid monoester, isethionate, imidazolinium derivatives, methyl taurate, sarcosinate, fatty acid amide ether sulfate, alkylamidobetaine, aliphatic alcohol, fatty acid glyceride, fatty acid diethanolamide, vegetable oil, lanolin derivative or ethoxylated glycerol fatty acid ester and the like.

Another aspect of the present disclosure provides a use of the pharmaceutical composition for preventing or treating inflammatory diseases.

Another aspect of the present disclosure provides a use of the pharmaceutical composition for preparing a medicament for the prevention or treatment of inflammatory diseases.

Another aspect of the present disclosure provides a method for preventing or treating inflammatory diseases, the method including administering the pharmaceutical composition.

Another aspect of the present disclosure provides a use of the cosmetic composition for preventing or alleviating dermatitis.

Another aspect of the present disclosure provides a use of the cosmetic composition for preparing cosmetic products for preventing or alleviating dermatitis.

Another aspect of the present disclosure provides a method for preventing or alleviating dermatitis, the method including applying the cosmetic composition.

EXAMPLES

Hereinafter, the present disclosure will be described in more detail based on Examples. However, Production Examples and Examples are for illustrative purposes only, and the scope of the present disclosure is not limited to these Examples.

I. Identification of Inhibitory Effect of Acylhydrazone Derivative Compound on Dermatitis Using Mice Having Induced Dermatitis on Back Portion Thereof Example 1. Visually Identifying Effect of Acylhydrazone Derivative Compound on Dermatitis Inhibition To demonstrate the anti-inflammatory effect of the acylhydrazone derivative compound, a mouse model having dermatitis induced by oxazolone was prepared. Specifically, 150 μl of 5% oxazolone (4-ethoxymethylene-2-phenyl-2-oxazolin-5-one) was applied to a back skin of a 6-week-old HR-1 (hairless) mouse, and then 150 μl of oxazolone (4-ethoxymethylene-2-phenyl-2-oxazolin-5-one) diluted into 0.1% was applied thereto 3 times a week, 11 times in total. Thus, the back skin inflammatory reaction was induced. Thereafter, 150 μl of the acylhydrazone derivative compound at a concentration of 500 nM was applied thereto 5 times a week, a total of 19 times. To verify the efficacy of the compound in a compared manner, Cyclosporine A which is widely known for anti-inflammatory effect was used as a comparative substance. A negative control treated with only ethanol as a solvent and a positive control treated with only oxazolone were reflected in the test. The number of mice in each test group was maintained at 10 or more, and the experiment was repeated twice.

As a result, it was identified that in the positive control treated only with oxazolone, dry skin was observed with red spots, and a typical skin inflammatory reaction was induced. On the other hand, in the test group treated with the acylhydrazone derivative compounds WCI-1004, WCI-1015, and WCI-1031 compounds or Cyclosporine A, skin conditions very similar to those of the negative control treated with ethanol as a solvent were observed. Thus, it was identified that the acylhydrazone derivative compound effectively inhibits the skin inflammatory response (FIG. 1).

Example 2. Identification of Inhibitory Effect of Acylhydrazone Derivative Compound on Expression of Inflammatory Cytokines Inflammatory cytokines most associated with development of dermatitis such as atopic dermatitis are known as IL-4 and IL-13 which are secreted primarily from Th2 T cells. To further identify the anti-inflammatory effect of the acylhydrazone derivative compounds in mice in which dermatitis is induced by oxazolone. A mRNA level of IL-2 as secreted from Th2 T cells and mRNA levels of IL-4 and IL-13 as the cytokines most closely related to the development of dermatitis in the inflammatory tissue were quantified.

Specifically, a skin tissue was collected from the dermatitis-induced mice produced in Example 1 and crushed using a tissue disruptor. The crushed tissue powder was dissolved in a solution of Trizol reagent (Sigma company), and RNA was extracted therefrom using an RNeasy mini kit (Qiagen company). The extracted RNA was reverse transcribed into cDNA using an ImProm-II™ Reverse Transcription kit (Promega company). Then, using a CFX96™ Real-Time PCR Detection System (Bio-Rad company), levels of the cytokines present in the skin tissue was measured based on a qPCR (quantitative PCR) method.

Figure 2A:
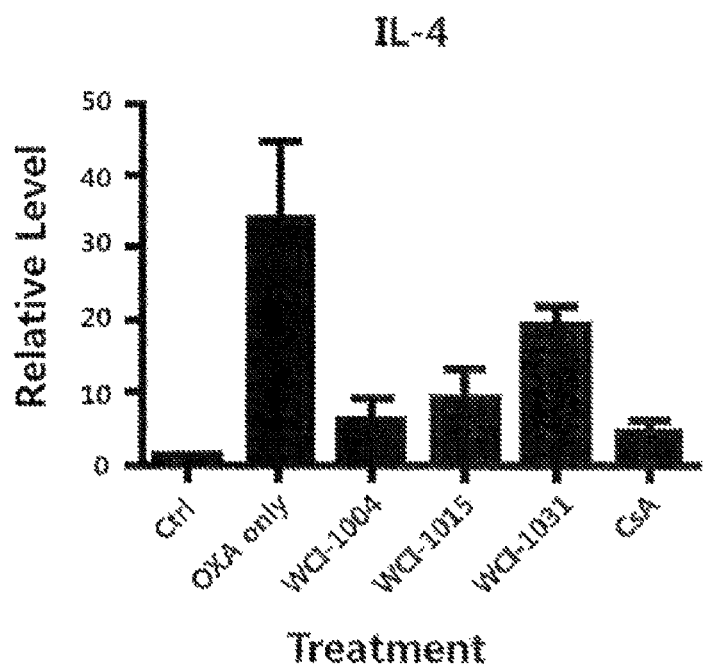
FIG. 2A is a figure showing an expression level of IL-4 in a skin tissue after administration of the acylhydrazone derivative compound or Cyclosporine A to a mouse having induced dermatitis on a back portion thereof.
Figure 2B:
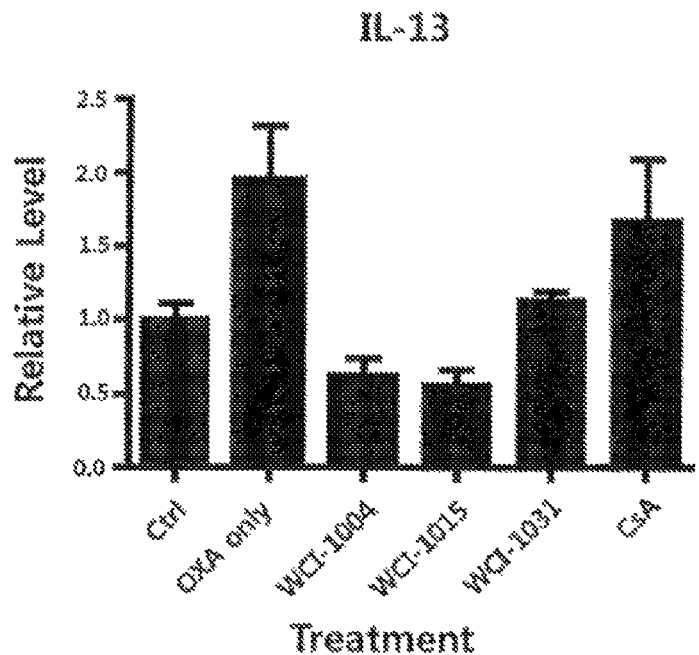
FIG. 2B is a figure showing an expression level of IL-13 in a skin tissue after the acylhydrazone derivative compound or Cyclosporine A is administered to mice having induced dermatitis on a back portion thereof.
Figure 2C:
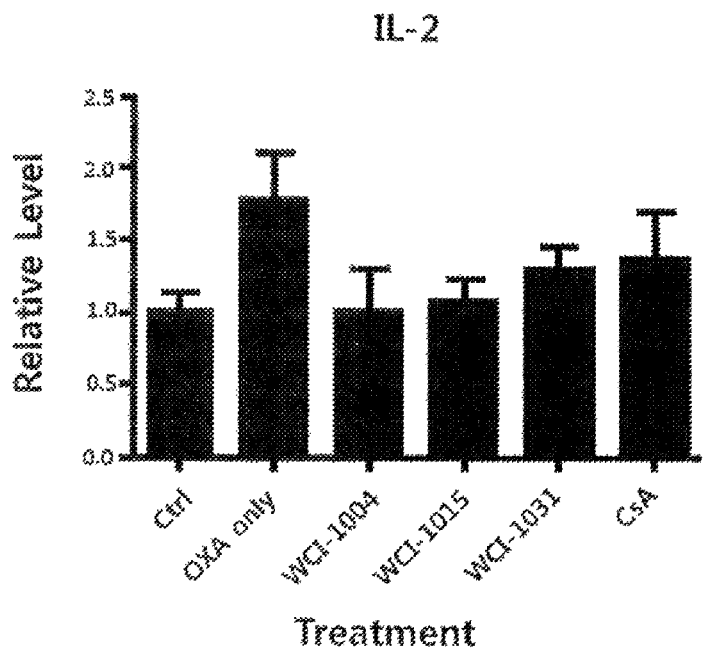
FIG. 2C is a figure showing an expression level of IL-2 in a skin tissue after the acylhydrazone derivative compound or Cyclosporine A is administered to a mouse having induced dermatitis on a back portion thereof.

As a result, the level of the inflammatory cytokines was significantly increased in the positive control treated with only oxazolone. On the other hand, it was identified that in the skin tissue of the test group treated with Cyclosporine A, WCI-1004, WCI-1015 or WCI-1031 compound, an expression level of the inflammatory cytokine was significantly reduced. In particular, the skin tissue of the test group treated with WCI-1004, WCI-1015 or WCI-1031 compound had lower levels of inflammatory cytokine expression than that in the skin tissue of the test group treated with Cyclosporine A. Thus, it was identified that the acylhydrazone derivative compound has a superior inflammatory cytokine inhibitory effect than Cyclosporine A has (FIG. 2A to FIG. 2C).

Example 3. Identification of Inhibitory Effect of Acylhydrazone Derivative Compound on Epithelial Hyperplasia When dermatitis is induced, a pathological symptom such as epidermal hyperplasia which thickens the skin is induced. To identify whether the acylhydrazone compound may relieve the dermatitis symptoms and maintain a skin homeostasis in oxazolone-induced inflammatory reactions, RNA was extracted from the skin tissue in the same manner as in Example 2, and then mRNA expression levels of K14 (Keratin 14), K1 (Keratin 1), and FLG (Filaggrin gene) were measured using a qPCR method.

As a result, the dermatitis-induced mice treated with oxazolone alone exhibited symptoms of the epidermal hyperplasia in which expression levels of K14 in a base layer of the skin, K1 in an upper layer of the skin, and FLG in a top layer of the skin increased (FIG. 3A). On the other hand, it was identified that in the skin tissue of the test group treated with Cyclosporine A, WCI-1004, WCI-1015 or WCI-1031 compound, expression levels of the above factors were restored to normal levels, and the epithelial hyperplasia symptoms were recovered (FIG. 3B to FIG. 3D).

Thus, the excellent anti-inflammatory and skin regeneration effects of the acylhydrazone derivative compounds were identified.

II. Identification of Effect of Acylhydrazone Derivative Compound on Dermatitis Inhibition in Mice with Induced Dermatitis in Ear Example 4. Visually Identifying Effect of Acylhydrazone Derivative Compound on Dermatitis Inhibition To demonstrate the anti-inflammatory effect of the acylhydrazone derivative compound, a mouse model having dermatitis induced by oxazolone was constructed. Specifically, 150 μl of 3% concentration of oxazolone was applied to an abdominal skin of a 6-week-old mouse to induce an immune response. 20 μl of the same compound diluted to 0.5% concentration was applied to the mouse's ear, total 5 times a day to induce an inflammatory reaction. Thereafter, at 30 minutes after the oxazolone application, 20 μl of each of the acylhydrazone derivative compounds was applied thereto at a concentration of 500 nM and total 5 times.

To compare and verify the efficacy of the compound, Cyclosporine A which is widely known for anti-inflammatory effect was used as a comparative substance. Moreover, the negative control treated only with ethanol as a solvent and the positive control treated only with oxazolone were reflected in the experiment. The number of mice in each test group was maintained at 10 or more, and the experiment was repeated twice.

As a result, it was identified that an ear of the positive control treated with oxazolone alone exhibited redness, compared to an ear treated with only ethanol as a solvent, and thus the inflammatory reaction was well induced. On the other hand, in the animal group treated with each of the acylhydrazone derivative compounds WCI-1004, WCI-1015 and WCI-1031 compounds and Cyclosporine A, a skin condition very similar to that of the negative control treated with ethanol was observed. Thus, it was identified that the acylhydrazone derivative compounds effectively suppress skin inflammatory reactions (FIG. 4).

Example 5. Identification of Inhibitory Effect of Acylhydrazone Derivative Compound on Dermatitis Via Histopathological Analysis For pathological observation of the skin after completion of the application experiment, an ear skin tissue of each mouse was collected and stained with Hematoxylin and Eosin.

Figure 5:
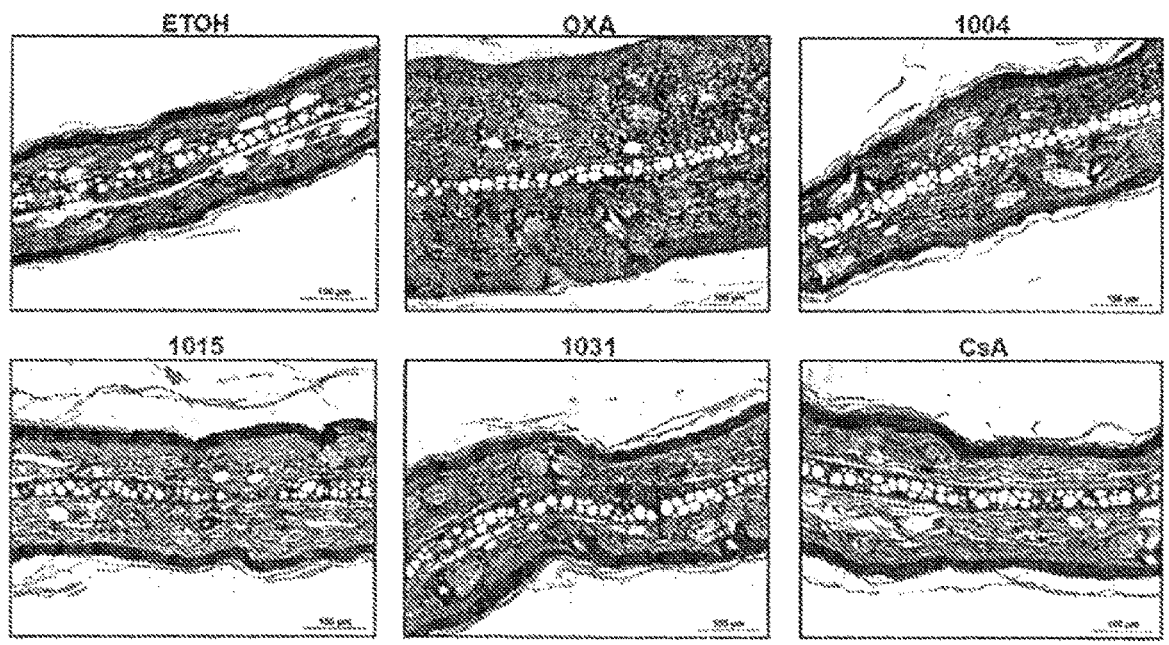
FIG. 5 is a photograph of a skin tissue stained with hematoxylin and eosin after administration of the acylhydrazone derivative compound or Cyclosporine A to a mouse having induced dermatitis in an ear.

As a result, usually, when dermatitis is induced, a pathological phenomenon of epidermal hyperplasia occurs. An ear skin tissue collected from the positive control treated with oxazolone alone had a total thickness increase by about 2 times compared to that of the negative control treated with ethanol alone. A thickness of the epithelium thereof increased by about 3 times, compared to that of the negative control treated with ethanol alone. On the other hand, it was identified that in an ear skin tissues taken from the test group treated with each of WCI-1004, WCI-1015, WCI-1031 compounds, or Cyclosporine A, each of an entire thickness of the skin and a thickness of the epithelium was reduced to a thickness very similar to that of the negative control. Thus, it was identified that the acylhydrazone derivative compound effectively inhibits skin inflammatory reactions (FIG. 5).

Example 6. Identification of Inhibitory Effect of Acylhydrazone Derivative Compound on Inflammatory Cytokine Expression Inflammatory cytokines most associated with the development of dermatitis, such as atopic dermatitis are known as IL-4 and IL-13 which are secreted primarily from Th2 T cells. In order to further identify the anti-inflammatory effect of the acylhydrazone derivative compound in mice with dermatitis induced by oxazolone in Example 4, an ear skin tissue was collected to quantify the mRNA levels of IL-2 secreted from Th2 T cells, along with those of IL-4 and IL-13.

Specifically, ear skin tissues were collected from dermatitis-induced mice prepared in Example 4 and crushed using a tissue disruptor. The crushed tissue powder was dissolved in a solution of Trizol reagent (Sigma company), and RNA was extracted using an RNeasy mini kit (Qiagen company). After reverse transcription of the extracted RNA with a cDNA using ImProm-II™ Reverse Transcription kit (Promega company), a level of cytokines present in a skin tissue was measured using a CFX96 Real-Time PCR Detection System (Bio-Rad company) via a qPCR method.

Figure 6A:
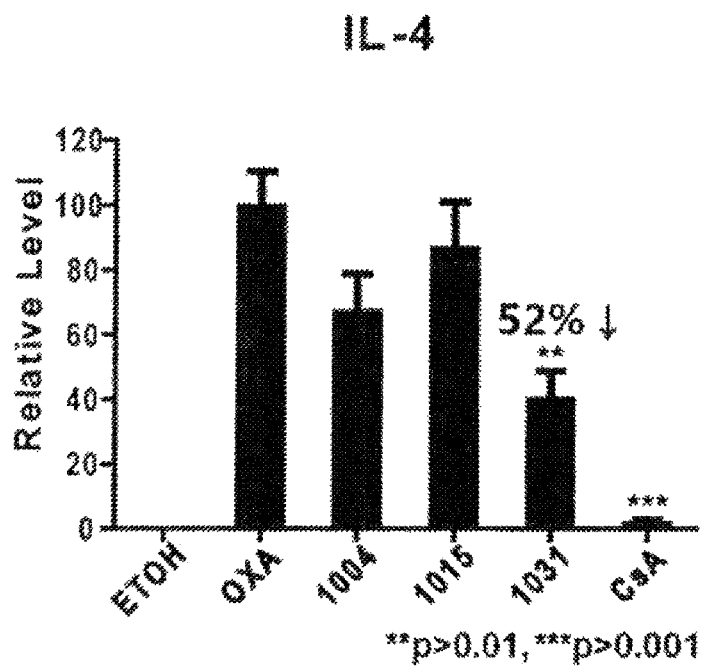
FIG. 6A is a figure showing an expression level of IL-4 in a skin tissue after the acylhydrazone derivative compound or Cyclosporine A is administered to a mouse having induced dermatitis in an ear.
Figure 6B:
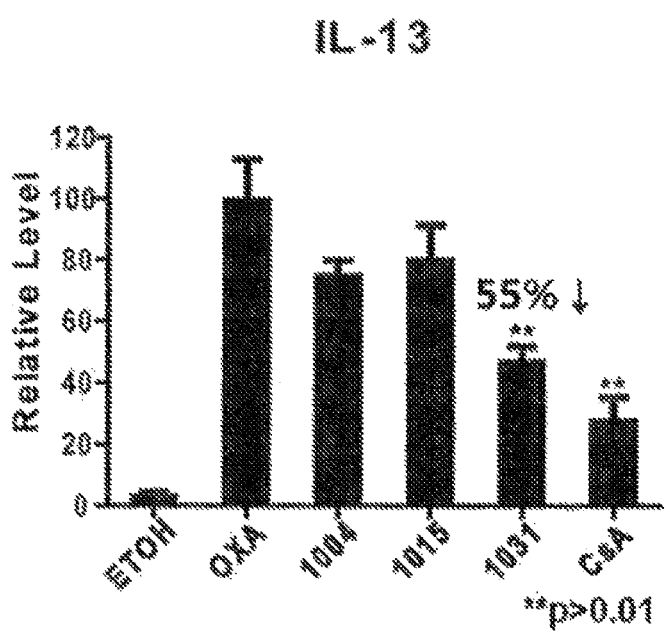
FIG. 6B is a figure showing an expression level of IL-13 in a skin tissue after the acylhydrazone derivative compound or Cyclosporine A is administered to a mouse having induced dermatitis in an ear.
Figure 6C:
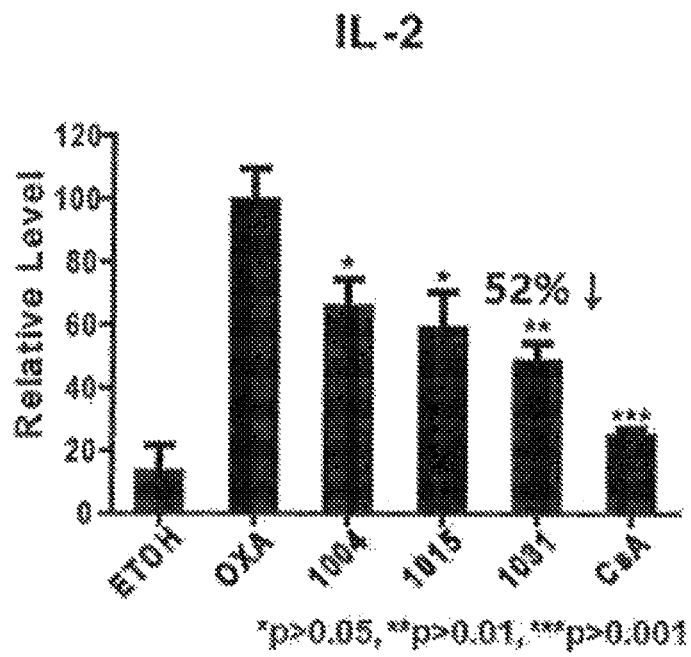
FIG. 6C is a figure showing an expression level of IL-2 in a skin tissue after the acylhydrazone derivative compound or Cyclosporine A is administered to a mouse having induced dermatitis in an ear.

As a result, an expression level of each of IL-4, IL-13 and IL-2 in the tissue was increased in an ear skin tissue of the positive control treated with oxazolone alone, compared to that in an ear skin tissue of the negative control treated only with ethanol. On the other hand, it was identified that the level of the cytokine expression in an ear skin tissue of the test group treated with WCI-1004, WCI-1015, WCI-1031 compounds or Cyclosporine A was significantly reduced to 50% of the cytokine expression level of the positive control. (FIG. 6A to FIG. 6C).

Example 7. Identifying Effect of Acylhydrazone Derivative Compound on Reducing Number of Inflammatory Immune Cells When dermatitis is induced, a pathological phenomenon in which the number of inflammatory immune cells in the entire skin is generally increased is observed. In order to further identify the anti-inflammatory effect of the acylhydrazone derivative compound in mice in which dermatitis was induced by oxazolone in Example 4, ear skin tissue was collected to measure the number of inflammatory immune cells.

Figure 7:
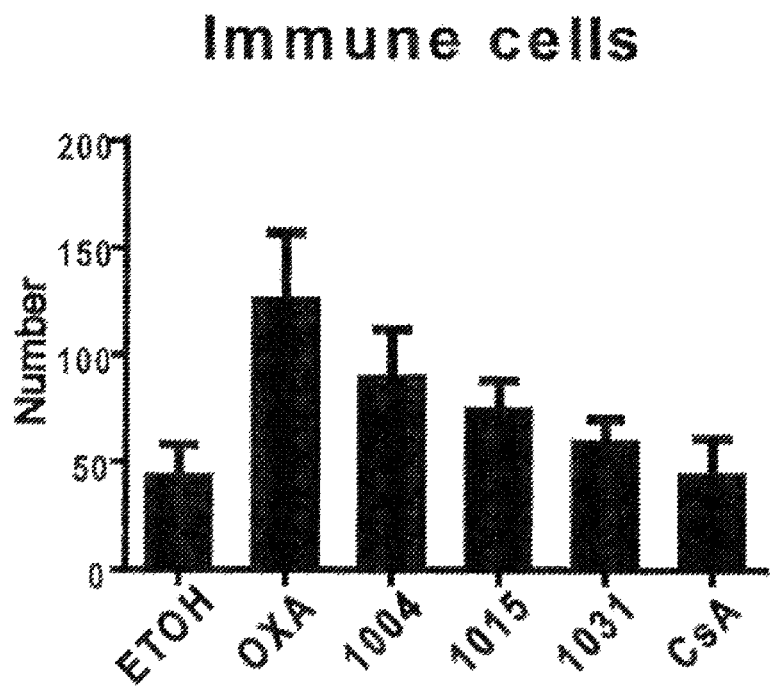
FIG. 7 is a figure of measuring the number of immune cells in a skin tissue after the acylhydrazone derivative compound or Cyclosporine A is administered to mice having induced dermatitis in an ear.

As a result, the number of inflammatory immune cells increased by about 3 times in an ear skin tissue of the positive control treated with oxazolone alone, compared to that in the skin tissue of the negative control treated only with ethanol. On the other hand, in an ear skin tissue of the test group treated with WCI-1004, WCI-1015, WCI-1031 compounds, or Cyclosporine A, inflammatory immune cell counts similar to that of the negative control were observed. Thus, it was identified that the acylhydrazone derivative compound reduces the number of inflammatory immune cells (FIG. 7).

Example 8. Identification of Inhibitory Effect of Acylhydrazone Derivative Compound on Epithelial Hyperplasia When dermatitis is induced, pathological symptoms such as epidermal hyperplasia which thickens the skin are induced. To identify whether the acylhydrazone derivative compound relieves dermatitis symptoms and maintains a skin homeostasis in a skin having an inflammatory reaction caused by oxazolone, RNA was extracted from the skin tissue in the same manner as in Example 6, and mRNA expression levels of K14 and K1 were measured using a qPCR method.

As a result, the epidermal hyperplasia symptoms in which expression levels of both K14 and K1 were increased was observed in an ear skin tissue of the positive control treated with oxazolone alone. On the other hand, each of expression levels of K14 and K1 in an ear skin tissues of the test group treated with WCI-1004, WCI-1015, WCI-1031 compounds or Cyclosporine A was restored to a normal level, and thus epithelial hyperplasia symptom was removed. Thus, it was identified that the acylhydrazone derivative compound had excellent anti-inflammatory effect and skin regeneration and homeostasis maintenance effect (FIG. 8A and FIG. 8B).

Example 9. Identification of Inhibitory Effect of Inflammatory Signaling Pathway by Acylhydrazone Derivative Compounds Using Immune Cell Lines To further identify the mechanism of action involved in the anti-inflammatory effect by the acylhydrazone derivative compound, RAW cell lines as mice-derived macrophage immune cell lines were incubated. We observed the effect of the compound according to the present disclosure on NF-κB (nuclear factor kappa-light-chain-enhancer of activated B cells) signaling pathway involved in the production of inflammatory cytokines. The NF-κB signaling pathway is involved in inflammatory reactions. In particular, it is known that when phosphorylation of p65 (RelA) is induced, phosphorylated p65 moves to the nucleus of immune cells and induces an expression of cytokines that cause inflammatory reactions.

Specifically, after incubating a predetermined amount of RAW cells ($5 \times 10^5$ to $10 \times 10^5$ cells/well for a 6-well plate) in DMEM medium (containing 10% fetal calf serum), WCI-1004, WCI-1015, and WCI-1031 compounds together with factors (tumor necrosis factor-α, lipopolysaccharide, or the like) inducing the NF-κB signal transduction were applied thereto for 12 to 24 hours. A proteolytic inhibitor and a dephosphorylation inhibitor was added to RIPA lysis and extraction buffer (Thermofisher company). Protein was extracted from the RAW cells. The Western blotting process used a method commonly used in the technical field to which the present disclosure belongs, and an antibody specific to phosphorylated p65 employed a product from Cell Signaling Technology company.

As a result, it was identified that when WCI-1004, WCI-1015 or WCI-1031 compound was administered to the macrophage immune cell line, phosphorylation of p65 (RelA) which is known to induce an immune response through the NF-κB signaling pathway involved in the production of inflammatory cytokines was effectively suppressed (FIG. 9).

Thus, it was identified that the acylhydrazone derivative compound effectively blocks the NF-KB signaling pathway associated with the inflammatory response.

The invention claimed is:

1. A method for treating dermatitis, comprising administering to a subject in need thereof an effective amount of a compound represented by a following Chemical Formula 1, a stereoisomer thereof, or a pharmaceutically acceptable salt thereof:

[Chemical Formula 1]

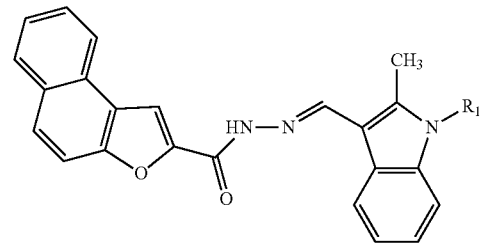

wherein in the Chemical Formula 1, $R_1$ is methyl or —(CH2)m(C=O)OR2, where R2 is methyl or ethyl, and m is 0, 1, 2 or 3.

2. The method of claim 1, wherein the compound represented by the Chemical Formula 1 is any one selected from following Chemical Formulas:

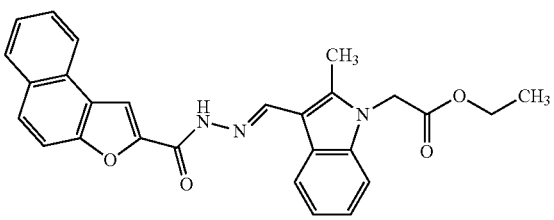

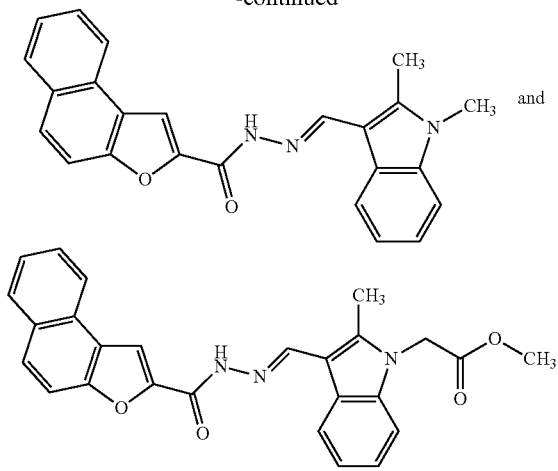

3. The method of claim 1, wherein the dermatitis is atopic dermatitis, contact dermatitis or allergic dermatitis.

4. The method of claim 1, wherein the compound suppresses an expression of inflammatory cytokines.

5. The method of claim 4, wherein the cytokine includes interleukin (IL)-2, interleukin-4 or interleukin-13.

6. The method of claim 1, wherein the compound suppresses a symptom of skin erythema or dry skin.

7. The method of claim 1, wherein the compound inhibits epidermal hyperplasia.

8. The method of claim 1, wherein the compound is administered transdermally or orally.

9. A method for alleviating skin inflammation caused by dermatitis, comprising applying to a subject in need thereof an effective amount of a compound represented by a following Chemical Formula 1, a stereoisomer thereof, or a pharmaceutically acceptable salt thereof:

[Chemical Formula 1]

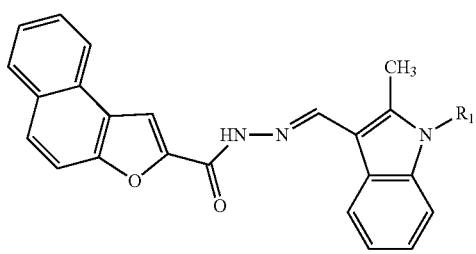

wherein in the Chemical Formula 1, $R_1$ is methyl or —(CH2)m(C=O)OR2, where R2 is methyl or ethyl, and m is 0, 1, 2 or 3.

10. The method of claim 9, wherein the compound represented by the Chemical Formula 1 is any one selected from following Chemical Formulas:

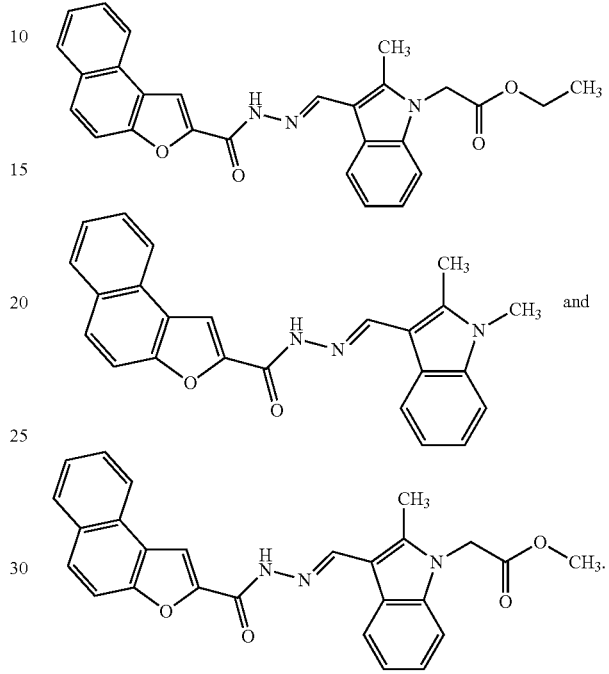

11. The method of claim 9, wherein the method for alleviating skin inflammation alleviates dermatitis in skin.

12. The method of claim 11, wherein the dermatitis is atopic dermatitis, contact dermatitis or allergic dermatitis.

13. The method of claim 9, wherein the method for alleviating skin inflammation suppresses a symptom of skin erythema or dry skin.

14. The method of claim 9, wherein the method for alleviating skin inflammation inhibits epidermal hyperplasia.

* * * * *